(12) United States Patent
Katoh et al.

(10) Patent No.: US 7,811,597 B2
(45) Date of Patent: Oct. 12, 2010

(54) GARBAGE BAG OR CONTAINER

(75) Inventors: Masahiko Katoh, Mie (JP); Joseph Dussich, Manhasset, NY (US)

(73) Assignee: JAD Corporation of America, College Point, NY (US)

( * ) Notice: Subject to any disclaimer, the term of this patent is extended or adjusted under 35 U.S.C. 154(b) by 1403 days.

(21) Appl. No.: 11/234,082

(22) Filed: Sep. 26, 2005

(65) Prior Publication Data

US 2006/0110421 A1     May 25, 2006

Related U.S. Application Data

(60) Provisional application No. 60/612,629, filed on Sep. 24, 2004.

(51) Int. Cl.

| | |
|---|---|
| *A01N 25/34* | (2006.01) |
| *A01N 25/00* | (2006.01) |
| *A01N 25/26* | (2006.01) |
| *A01N 35/00* | (2006.01) |
| *A01N 35/04* | (2006.01) |
| *A61K 9/14* | (2006.01) |
| *A61K 31/12* | (2006.01) |
| *A61K 31/125* | (2006.01) |

(52) U.S. Cl. .............. 424/403; 424/405; 424/412; 424/419; 424/486; 514/689; 514/690; 514/692

(58) Field of Classification Search ............... 428/35.5; 424/403, 405, 411–412, 419, 485–486; 514/689, 514/690, 692

See application file for complete search history.

(56) References Cited

U.S. PATENT DOCUMENTS

| | | | | |
|---|---|---|---|---|
| 5,041,421 A | * | 8/1991 | King | ........................ 512/4 |
| 5,571,582 A | * | 11/1996 | Katoh | ........................ 428/35.5 |

* cited by examiner

*Primary Examiner*—Johann R Richter
*Assistant Examiner*—Mei-Ping Chui
(74) *Attorney, Agent, or Firm*—Harris Beach PLLC; Todd S. Sharinn

(57) ABSTRACT

An article, such as a container or bag for garbage, which repels animals such as cats, dogs, rats, and crows. The article may be made from a synthetic resin composition including a synthetic resin and from 10 to 15,000 ppm by weight of a salicylic acid ester, menthol and/or camphor. The article may also be made from a synthetic resin composition including a synthetic resin and an odorant composition containing eucalyptus oil and one or more of a salicylic acid ester, menthol and camphor.

10 Claims, No Drawings

GARBAGE BAG OR CONTAINER

This application claims benefit of Provisional Application No. 60/612,629, filed Sep. 24, 2004, the disclosure of which is incorporated herein by reference.

BACKGROUND OF THE INVENTION

The present invention relates to a synthetic resin composition which continues, for a relatively long time, to shed an odor that keeps away domesticated animals, especially cats and dogs, and also varmints of both fur and feather, for example rats, crows, etc. The invention also relates to articles, such as garbage bags, containers, or cable insulation, into which the synthetic resin composition may be easily shaped.

A number of repellents are known, but none of them is satisfactory both in terms of effect and cost. In addition, in most cases they are used in either of the following methods. They are either impregnated into a powdery support and spread or sprayed directly on an article. Furthermore, manufacturing shaped articles having a repellent effect by shaping a synthetic resin composition containing a repellent has not yet been put into practice.

In many cities, the disposal of residential garbage is carried out as follows. Each household puts its garbage into a polyethylene garbage bag designated by the city and places the filled bag in the designated spot outside on the appointed day. The garbage bags are then collected by city garbage trucks.

A problem associated with this conventional disposal method is that garbage bags left outside are often ripped by animals like cats and dogs before garbage trucks can collect them, thereby scattering the garbage.

Also, there are problems with cable insulation. Cable, such as electrical cable, insulated with an insulator made from synthetic resin is often laid in the ceiling or under the floor where it is susceptible to being bit by rats. As a result, electricity leakage, short-circuits, etc. may take place.

Thus, it is a prime object of this invention to provide a synthetic resin composition which may be easily shaped into garbage bags, containers, cable insulation, etc. and which is not unpleasant for people but has enough of a repellent effect to keep away domesticated animals, especially cats and dogs, and also varmints of both fur and feather, for example rats, crows, etc.

SUMMARY OF THE INVENTION

The synthetic resin composition of this invention contains a synthetic resin and 10 to 15,000 ppm by weight, based on the total weight of the composition, of at least one compound selected from the group consisting of a salicylic acid ester, menthol and camphor. Examples of suitable salicylic acid esters include methyl salicylate, ethyl salicylate, propyl salicylate, n-butyl salicylate, iso-butyl salicylate and iso-amyl salicylate.

The synthetic resin to be used in the invention is not particularly limited. Thermoplastic polymers, especially polyolefins, such as polyethylene, polypropylene, ethylene/vinyl acetate copolymer, ethylene/acrylic acid ester copolymer and poly(1-butene), which are used for manufacturing daily necessities such as garbage bags and containers are preferable. The synthetic resin composition of the invention can be shaped into various articles, such as bags, bottles etc. by a variety of methods, including, for example, extrusion, injection and blow molding.

The inventor has discovered that animals, including cats, dogs, rats and crows, dislike the particular odor of salicylic acid esters, menthol and camphor. The invention uses this characteristic of salicylic acid esters, menthol and camphor to provide shaped articles with a repellent effect by incorporating the odorants into the synthetic resin prior to forming the shaped articles. Thereafter, the shaped article effectively prevents animals from ripping the articles.

It was found that the repellent effect was observed if shaped articles contained more than 1 ppm by weight, based on the total weight of the composition, of these odorants. However, it may be necessary for the synthetic resin composition itself to contain more than 10 ppm by weight, based on the total weight of the composition, of the odorant(s) in consideration of loss caused by the shaping. Furthermore, from the view point of obtaining both a sufficient and durable repellent effect, the concentration of the odorant(s) should be high, but if the concentration is higher than 15,000 ppm, based on the total weight of the composition, unwanted bleeding may occur. In order to obtain the best result, the concentration is preferably 10 to 15,000 ppm by weight, based on the total weight of the composition, more preferably 1,000 to 15,000 ppm by weight, most preferably 7,500 to 14,000 ppm by weight.

Preferably, an elastomer, especially an elastomer that is miscible with the odorant(s), or a filler, preferably having the ability to adsorb the odorant(s), is added to the synthetic resin composition of the invention in order to slow and prolong the shedding of the odorant, such that a shaped article comprising this preferred embodiment of the composition can keep animals away for a longer period of time.

If the concentration of the elastomer in the synthetic resin composition is lower than 1% by weight, based on the total weight of the composition, shedding of the odorant is not significantly prolonged. Concentrations of the elastomer higher than 50% by weight, based on the total weight of the composition, do not significantly improve the duration of shedding in comparison to an elastomer concentration of 50% by weight.

If the concentration of the filler in the synthetic resin composition is lower than 0.1% by weight, based on the total weight of the composition, shedding of the odorant may not be significantly prolonged. Concentrations of the filler higher than 60% by weight, based on the total weight of the composition, may not significantly improve the duration of shedding in comparison to a filler concentration of 60% by weight.

As mentioned, the synthetic resin to be used in the invention is not particularly limited. However, ethylene/vinyl acetate copolymer, ethylene/acrylic acid ester copolymer, or ethylene/ethyl acrylate copolymer (E/EA), each of which has a lower crystallinity than a homopolymer, may be used as the synthetic resin of the composition of the invention in order to further slow and prolong the shedding of the odorant.

DETAILED DESCRIPTION OF THE INVENTION

More specific examples of the synthetic resin to be used in the invention include linear low density polyethylene (LLDPE), high pressure low density polyethylene (HPLDPE), and high density polyethylene (HDPE).

Specific examples of the elastomer to be used in preferred embodiments of the invention include ethylene/propylene rubber (EPR), very low density polyethylene (VLDPE), hydrogenated styrene/butadiene block copolymer (SEBS), polybutadiene, ethylene/ester of acrylic acid copolymer, ethylene/butene copolymer, ethylene/1-hexene copolymer, ethylene/1-octene copolymer, butadiene/styrene copolymer, isoprene/styrene copolymer, and hydrogenated isoprene/styrene copolymer.

Specific examples of the filler to be used in preferred embodiments of the invention include diatomaceous earth, silica gel, synthetic zeolite, aluminum oxide, hydrotalcite, calcium carbonate, talc, natural zeolite, wollastonite, calcium sulfate, magnesium hydroxide, aluminum hydroxide, titanium dioxide, and carbon black.

Articles, including garbage bags, containers, and cable insulation, may be formed from the synthetic resin composition of the invention by any of the procedures known in the art.

For example, the odorant may be incorporated into the synthetic resin composition by dropwise addition of a predetermined amount of the odorant onto pellets of the synthetic resin to be used. Thereafter, the pellets may be left alone for a predetermined amount of time at a predetermined temperature such that the odorant is impregnated into the pellets. The thus treated pellet may be mixed with untreated pellets to adjust the concentration of the odorant to the desired level.

Preferably, the pellets treated with the odorant are left alone for a period of time ranging from several hours to 24 hours in order to have the odorant impregnated therein. Preferably, the pellets treated with the odorant are left alone at room temperature.

As an alternative to the dropwise addition of a predetermined amount of the odorant onto pellets of the synthetic resin, pellets of the synthetic resin may be soaked in the liquid form of the odorant.

As an alternative to both dropwise addition and soaking in liquid odorant, a predetermined amount of odorant may be dissolved in a solvent, such as diethyl ether, and sprayed onto pellets of the synthetic resin. The solvent may be thereafter eliminated by, e.g., air-drying at room temperature.

The mixed pellets may be formed into blown film, as is known in the art. For example, the mixed pellets may be formed into blown film by inflation processing at 180° C. The blown film may thereafter be cut and formed into bags by bottom sealing.

Alternatively, the mixed pellets may be extruded and pelletized. The thus obtained homogenized composition may be formed into strips of film by compression molding.

The concentration of the odorant in the final article may be determined by head space gas chromatography, as is known in the art.

In certain embodiments, the synthetic resin composition may include one or both of eucalyptus oil and mint oil as part of its odorant composition. For example, in certain embodiments, the synthetic resin composition may include an odorant composition containing methyl salicylate, mint oil, camphor oil, and eucalyptus oil. In certain preferred embodiments, the synthetic resin composition may include an odorant composition containing from 32 to 40% by weight of methyl salicylate, from 32 to 40% by weight of mint oil, from 19 to 27% by weight of camphor oil, and from 1 to 8% by weight of eucalyptus oil, based on the total weight of the odorant composition.

For embodiments of the composition employing an elastomer, the pellets of synthetic resin to be treated with odorant may be combined with pellets of the elastomer to form a polymer blend of synthetic resin and elastomer. For example, the pellets to be treated with odorant may be a blend of 90% by weight synthetic resin and 10% by weight elastomer, based on the total weight of the pellets.

For embodiments of the composition employing a filler, a solution of the odorant and suitable solvent (e.g., diethyl ether) may be sprayed onto the filler. The solvent may thereafter be eliminated by air-drying at room temperature. Coated filler may then be added to treated or untreated pellets of the synthetic resin to obtain the desired concentration of odorant in the synthetic resin composition.

What is claimed is:

1. An article that repels animals, comprising a synthetic resin composition comprising:
   (i) a thermoplastic polymer; and (ii) 7,500 to 15,000 ppm by weight, based on the total weight of the synthetic resin composition, of at least one compound selected from the group consisting of a salicylic acid ester, menthol and camphor.

2. The article of claim 1, further comprising 1 to 50% by weight, based on the total weight of the synthetic resin composition, of an elastomer selected from the group consisting of ethylene/propylene rubber (EPR), very low density polyethylene (VLDPE), hydrogenated styrene/butadiene block copolymer (SEBS), polybutadiene, ethylene/ester of acrylic acid copolymer, ethylene/butene copolymer, ethylene/1-hexene copolymer, ethylene/1-octene copolymer, butadiene/styrene copolymer, isoprene/styrene copolymer, hydrogenated isoprene/styrene copolymer, and mixtures thereof.

3. The article of claim 1, further comprising 1 to 60% by weight, based on the total weight of the synthetic resin composition, of a filler selected from the group consisting of diatomaceous earth, silica gel, synthetic zeolite, aluminum oxide, hydrotalcite, calcium carbonate, talc, natural zeolite, wollastonite, calcium sulfate, magnesium hydroxide, aluminum hydroxide, titanium dioxide, and carbon black.

4. The article of claim 3, further comprising 1 to 50% by weight, based on the total weight of the synthetic resin composition, of an elastomer selected from the group consisting of ethylene/propylene rubber (EPR), very low density polyethylene (VLDPE), hydrogenated styrene/butadiene block copolymer (SEBS), polybutadiene, ethylene/ester of acrylic acid copolymer, ethylene/butene copolymer, ethylene/1-hexene copolymer, ethylene/1-octene copolymer, butadiene/styrene copolymer, isoprene/styrene copolymer, hydrogenated isoprene/styrene copolymer, and mixtures thereof.

5. The article of claim 1, wherein the thermoplastic polymer comprises a polyolefin.

6. The article of claim 5, wherein the polyolefin comprises polyethylene, polypropylene, ethylene/vinyl acetate copolymer, ethylene/acrylic acid ester copolymer, poly(1-butene), or ethylene/ethyl acrylate copolymer (E/EA).

7. The article of claim 1, wherein the synthetic resin composition comprises 7,500 to 14,000 ppm by weight, based on the total weight of the synthetic resin composition, of at least one compound selected from the group consisting of a salicylic acid ester, menthol and camphor.

8. The article of claim 1, wherein the synthetic resin composition further comprises eucalyptus oil.

9. The article of claim 1, wherein the article is a garbage bag.

10. The article of claim 1, wherein the article is cable insulation.

* * * * *